US012102149B2

United States Patent
Beach et al.

(10) Patent No.: US 12,102,149 B2
(45) Date of Patent: Oct. 1, 2024

(54) GARMENT

(71) Applicant: Splash About International Limited, Lincolnshire (GB)

(72) Inventors: Lesley Beach, Lincolnshire (GB); Brigit Cheeseman, Lincolnshire (GB); Bernadette Spofforth, Chester (GB)

(73) Assignee: Splash About International Limited, Lincolnshire (GB)

( * ) Notice: Subject to any disclaimer, the term of this patent is extended or adjusted under 35 U.S.C. 154(b) by 631 days.

(21) Appl. No.: 17/278,883

(22) PCT Filed: Sep. 24, 2019

(86) PCT No.: PCT/GB2019/052692
§ 371 (c)(1),
(2) Date: Mar. 23, 2021

(87) PCT Pub. No.: WO2020/065299
PCT Pub. Date: Apr. 2, 2020

(65) Prior Publication Data
US 2022/0047025 A1  Feb. 17, 2022

(30) Foreign Application Priority Data
Sep. 24, 2018 (GB) ..................... 1815537

(51) Int. Cl.
*A41D 31/30* (2019.01)
*A41D 7/00* (2006.01)
*A41D 31/10* (2019.01)

(52) U.S. Cl.
CPC ........... *A41D 31/305* (2019.02); *A41D 7/005* (2013.01); *A41D 31/10* (2019.02); *A41B 2400/34* (2013.01)

(58) Field of Classification Search
CPC ...... A61F 13/15; A61F 13/496; A61F 13/494; A61F 13/04; A61F 13/15203;
(Continued)

(56) References Cited

U.S. PATENT DOCUMENTS 6,797,856 B1 * 9/2004 Kolb ................... A61F 13/496
604/385.03
6,823,530 B2   11/2004 Quincy, III
(Continued)

FOREIGN PATENT DOCUMENTS

CA   3 036 923      3/2018
CN   203724340 U   7/2014
(Continued)

*Primary Examiner* — Camie S Thompson
(74) *Attorney, Agent, or Firm* — Salter & Michaelson

(57) ABSTRACT

A garment, particularly swimwear, to cover a wearer's body between the waist and thighs has a shell of substantially impermeable material, a permeable inner lining material which lies next to the wearer's skin in use and an antimicrobial agent disposed between the shell of substantially impermeable material and the inner lining material. The antimicrobial agent may be Silver which has been deposited by a physical deposition process onto a textile disposed between the shell and inner lining material. The garment may form a lining of a swim nappy, the combination providing an article of swimwear.

19 Claims, 8 Drawing Sheets

Figure 1:
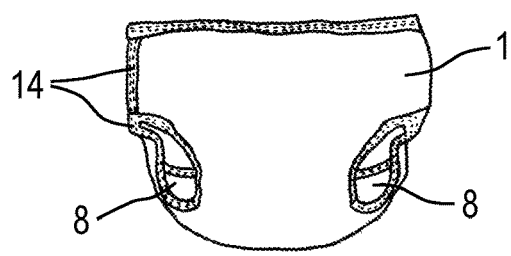

(58) Field of Classification Search
CPC .......... A61F 13/49006; A61F 13/51405; A61F 13/49009; A61F 13/51113; A61F 13/8405; A41D 31/10; A41D 31/305; A41D 7/005; A41D 31/01; A41D 7/00; A41D 31/30; A41B 2400/34
USPC .......... 604/385.23, 385.25, 385.01, 385.101, 604/385, 384; 442/394, 398, 123
See application file for complete search history.

(56) References Cited

U.S. PATENT DOCUMENTS

| | | |
|---|---|---|
| 7,344,526 B2 | 3/2008 | Yang et al. |
| 2002/0077612 A1 | 6/2002 | Quincy, III |
| 2005/0064020 A1 | 3/2005 | Schuette et al. |
| 2005/0125879 A1 | 6/2005 | Yang et al. |
| 2013/0152277 A1 | 6/2013 | Rakitin |
| 2013/0261580 A1* | 10/2013 | Gilmer .................... A61L 15/18 604/385.29 |
| 2014/0039432 A1 | 2/2014 | Dunbar et al. |
| 2016/0338884 A1* | 11/2016 | Quincy ................ A61F 13/496 |
| 2018/0087191 A1 | 3/2018 | Threlkeld |

FOREIGN PATENT DOCUMENTS

| | | | |
|---|---|---|---|
| EP | 2 433 600 | | 3/2012 |
| JP | 2004027379 | * | 1/2004 |
| KR | 101956752 | | 3/2019 |
| WO | 2012/038098 | | 3/2012 |
| WO | 2013/148749 | | 10/2013 |
| WO | 2014/176677 | | 11/2014 |
| WO | 2015/100440 | | 7/2015 |

* cited by examiner

GARMENT

TECHNICAL FIELD OF THE INVENTION

The present invention relates to a garment and particularly, but not exclusively, to swimwear, a swim nappy or diaper and/or a liner for swimwear or a swim nappy or diaper.

BACKGROUND TO THE INVENTION

Swim nappies are worn by babies and very young children learning to swim, and are intended to contain any faecal matter discharged by the wearer whilst in a swimming pool so as to minimise contamination of the pool.

In practice, current swim nappies are not 100% effective in retaining faecal matter as it is difficult to obtain a good seal between the nappy and a wearer whilst producing a garment that is safe and comfortable to wear. Consequently, bacteria and other pathogens present in faecal matter can and do find their way into swimming pool water. This is undesirable.

In an attempt to address this problem various swim nappies have been proposed which incorporate an antimicrobial agent in an attempt to kill bacteria and other pathogens in faecal matter released into the nappy, and thus avoid contamination of swimming pool water. For example, US2013/0261580 discloses a swim garment in the form of a brief. The garment is formed from a single layer of breathable, non-absorbent, non-woven material composed of a plastic film laminated to a non-woven textile support layer which has been treated with a Silver based antimicrobial solution. Similarly, CN202504215U discloses swimming trunks formed from an outer waterproof layer and an inner antibacterial textile layer intended to prevent bacteria from entering a wearer's skin.

In practice, existing garments incorporating an antimicrobial agent have proved ineffective at sufficiently neutralising harmful bacteria (in particular Cryptosporidium) to reduce swimming pool contamination to a safe level. In seeking to provide an improved garment, though, the applicant has realised that it may be undesirable for garments coated with certain more effective antimicrobial agents to be worn next to the skin, as they may cause discomfort, and that over time some Silver containing antimicrobial agents discolour making a garment unattractive to a user.

Embodiments of the present invention seek to address the above problems and it is an object of these embodiments to reduce (or eliminate) pathogens present in faecal matter discharged by a wearer entering swimming pool water.

SUMMARY OF THE INVENTION

According to a first aspect of the present invention there is provided a garment intended, in use, to cover a wearer's body between the waist and thighs, the garment comprising a shell of substantially impermeable material, a permeable inner lining material which lies next to the wearer's skin in use and an antimicrobial agent disposed between the shell of substantially impermeable material and the inner lining material.

The garment is useful as swimwear and its shell of substantially impermeable material helps to contain faecal or other matter discharged by a wear into the garment where bacteria or other pathogens can be destroyed or rendered harmless by the antimicrobial agent. Disposing the antimicrobial agent between the shell and inner lining allows a greater freedom of choice in choosing an appropriately effective antimicrobial material, whilst not compromising the comfort or safety of the wearer.

The shell may be formed from a textile material. It may be coated to render it substantially impermeable. The textile may be woven. The textile may be formed from a synthetic yarn such a nylon. The textile may be formed from a yarn of 60 to 80 denier, preferably about 70 denier and have a thread count of between 170 and 210, preferably about 190. The shell may form the outside of the garment.

The garment may take the form a brief having waist and leg openings. The openings may be elasticated. The shell may be formed from one, two or more panels. In one embodiment it is formed a single panel connected together at each side of the garment. At one or both sides of the garment the panels may be releasably connected, for example by hook and loop tape or some other suitable fastening.

The inner lining material may be formed from a textile material, which may be knitted. It may be formed from a synthetic yarn, such as polyester yarn, preferably a multifilament yarn. The yarn may have a denier between 40 and 50. The textile may have a mass in the range 170 to 115 grams per square metre (gsm) and is preferably about 125 gsm.

The antimicrobial agent may be inorganic. The antimicrobial agent may be a metal and may comprise one or more of Silver, Titanium, Germanium, Zinc and Copper. The agent may consist substantially of Silver.

The antimicrobial agent may be disposed on a textile material. This textile may be an additional textile positioned between the shell and inner lining of the garment. The antimicrobial agent may be coated onto the textile material by a physical deposition process, such as vacuum deposition, and, accordingly, the invention also includes a method of manufacture of a garment involving the step of coating an antimicrobial agent onto a textile or a yarn for forming a textile using such a process and either of which is subsequently used in the manufacture of the garment. Suitable deposition processes are described in CN100357515.

The antimicrobial agent may make up least 0.5%, 1%, 1.5%, 2%, 2.5% or 3% by weight of the textile material. In one preferred embodiment the antimicrobial agent is Silver and makes up between 1% and 3%, and preferably about 2%, by weight of the textile.

The textile on which the antimicrobial agent is provided may be knitted. It may be formed from multifilament yarn of between 130 and 170 denier. It may have a mass in the range 100 to 150 gsm. It may be formed from a synthetic yarn, a suitable yarn being polyester.

The textile on which the antimicrobial agent may be provided may be positioned at least within a crotch region of the garment and/or adjacent waist and leg openings of the garment.

According to a second aspect of the invention there is provided swimwear comprising an outer garment intended, in use, to cover a wearer's body at least between the waist and thighs, and an inner garment also intended, in use, to cover a wearer's body between the waist and thighs, the inner garment comprising an antimicrobial agent and being attached to the outer garment.

The inner garment may be a garment according to the first aspect of the invention.

The inner garment is attached to the outer garment in any suitable way and at an suitable point or points. In one embodiment the inner garment is attached to the outer garment partially or wholly around the waist of the inner garment.

The inner garment may be permanently attached to the outer garment. The inner garment may be stitched to the outer garment. The inner garment may be releasably attached to the outer garment, such as by one or more releasable fasteners.

The inner garment is preferably sized such that it is contained within the outer garment. The outer garment may comprise a body of substantially impermeable material and elasticated waist and leg bands. In this case the inner garment is preferably sized to sit within the body of the outer garment. Leg and waist openings of the inner garment may thus coincide or sit just within corresponding leg and waist openings of the body of the outer garment. This way, elasticated openings to the inner and elasticated leg and waist bands of the outer garment separately contact a wear and form a partial seal against the wearer against passage of matter into and out of the garment as a whole.

The outer garment may be formed from substantially impermeable panels. It may comprise a waist band formed from one or more panels of material. The waist band may have a top edge and bottom edge. The top edge may be shorter than the bottom edge. The bottom edge may be joined to a top edge of the remainder of the outer garment. The outer garment may further comprise two rear panels. These may be joined together along adjacent curved edges. The outer garment may be shaped so that, in use, the top edge of the waist band at the rear of the outer garment extends beyond the top edge of the waist band at the front of the outer garment so that the outer garment extends further up the wearer's back than the wearer's front.

The top edge of the back of the outer garment may be convex. The top edge of the front of the outer garment may be concave. The top edge of the outer garment may form a smooth curve around its periphery.

The waist band may have a substantially constant depth. The waist band may be formed from two or more panels of material, for example a fabric. One or more panels of material forming the waist band may be substantially trapezoidal in shape and the shorter parallel side or sides of the panels may form the top edge of the waist band.

The waist band may be formed from a resiliently stretchable fabric. The fabric may be of a type known as a high stretch fabric. It may be a knitted, such as tricot knit, fabric or a woven fabric. It may include a proportion of elastic fibre such as a natural or synthetic rubber, e.g. elastane (spandex). It may comprise at least 20% or at least 25% elastic fibre. The remainder may be a natural or synthetic fibre, such as nylon.

The top edge of the front of the remainder of the outer garment may be concave and/or the top edge of the rear of the remainder of the outer garment may be convex. That is to say, the shape of the ultimate top edge of the outer garment is created by the shape of the top edge of the remainder of the outer garment and not the waist band.

Alternatively it is possible for the waist band to be shaped to create and/or contribute to the desired shape of the top edge of the outer garment. As such the waist band may comprise a rear portion having a convex top edge and/or a front portion comprising a concave top edge.

The two rear panels may be mirror opposites and may be joined together along adjacent opposed curved edges. The opposed curved edges may have both concave and convex portions. Shaping the rear panels in this way enables the outer garment to better fit to the contours of a wearer's buttocks.

The outer garment may comprise a front panel having opposite side edges each joined to a respective side edge of a rear panel.

The outer garment may comprise a crotch panel intended to extend between a wearer's legs in use.

The front, rear and crotch panels may themselves be formed by a single panel or two or more panels joined together to produce a panel of desired overall shape. The panels may be formed from a resiliently stretchable material. The panels may be formed from a sheet material laminated with a fabric on one or both sides. The panels may be formed from a material with a higher elastic modulus than material forming waist and/or leg bands.

The crotch panel may be joined to a lower edge of each rear panel, and a lower edge of any front panel.

Panels of the outer garment may be joined together by any suitable means. Stitching is suitable. Panels may be joined with their adjacent edges abutting, such as by using flat lock stitching. Or panels may be joined by a seam, ideally positioned to the inside of the outer garment. Other joining techniques could of course be used such as using an adhesive or welding.

The waist band may extend above the top edge of the outer garment by a distance which is at least 10%, 15%, 20%, 25% or 30% of the shortest distance between a point on a lower edge of the front or rear panel to which the crotch panel is joined and a top edge of the front or rear panel at which the waist band is joined. The greater the depth (or width) of the waist band the more effectively it can help contain material within the outer garment, in use. For example, for a outer garment intended to be worn by a baby or infant under the age of 3 years the waist band preferably has a depth of at least 5, 6, 7 or 8 cm.

The outer garment may comprise leg bands which may be resiliently stretchable and may be formed from the same material as the waist band as discussed above.

A seal may be disposed around the inside of each leg opening and or waist opening arranged to form a seal with a wearer's body, in use. The seal may be formed by a strip of sealing material, such as a strip of natural or synthetic rubber or silicone rubber.

The outer garment may have the form of a brief or a pair of shorts or trunks.

According to a third aspect of the invention there is provided a method of manufacture of swimwear comprising the steps of:
  providing a yarn or textile;
  coating said yarn or textile with an antimicrobial agent using a vacuum deposition process;
  where present, forming the yarn into a textile;
  forming a garment which includes the coated textile.

According to a fourth aspect of the invention there is provided swimwear comprising a fabric having a coating of a microbial agent applied by a physical deposition process, such as by vacuum deposition.

The antimicrobial agent may be Silver and the coated textile may comprise at least 0.5%, 1%, 1.5%, 2%, 2.5% or 3% by weight of Silver. In one preferred embodiment Silver makes up between 1% and 3%, and preferably about 2%, by weight of the textile. The coated textile material is formed from multifilament yarn of between 130 and 170 denier and/or has a mass in the range 100 to 150 gsm.

The coated textile may be positioned at least within a crotch region of the garment and adjacent waist and leg openings of the garment.

According to another aspect of the invention there is provided a method of reducing contamination of a swimming pool by a swimmer comprising a swimmer wearing a garment according to either the first or fourth aspects of the invention, and wearing a swim nappy over that garment, the swim nappy comprising a body of substantially impermeable material and elasticated waist and leg bands or wearing swimwear according to the second aspect of the invention.

Garments according to all aspects of the invention may be made from materials which may be washed allowing the garments to be re-used.

DETAILED DESCRIPTION OF THE INVENTION

Figure 2:
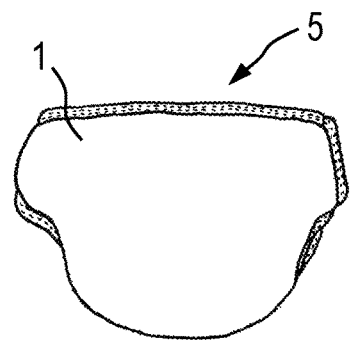
Figure 3:
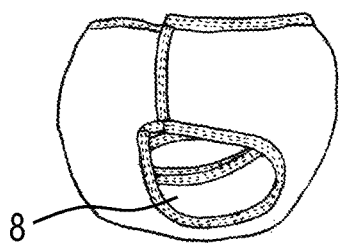
Figure 4:
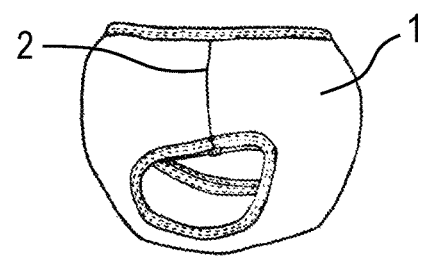
Figure 5:
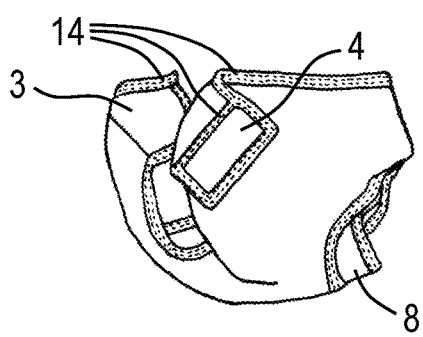
Figure 6:
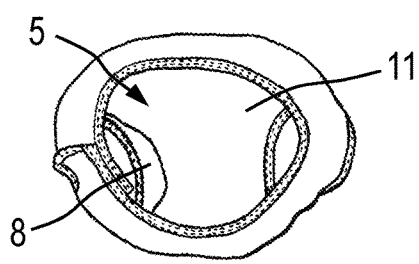
Figure 7:
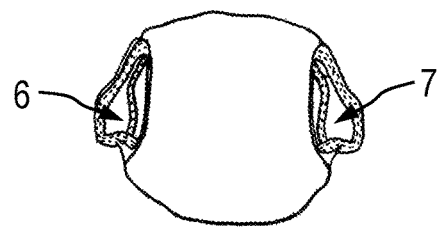
Figure 8:
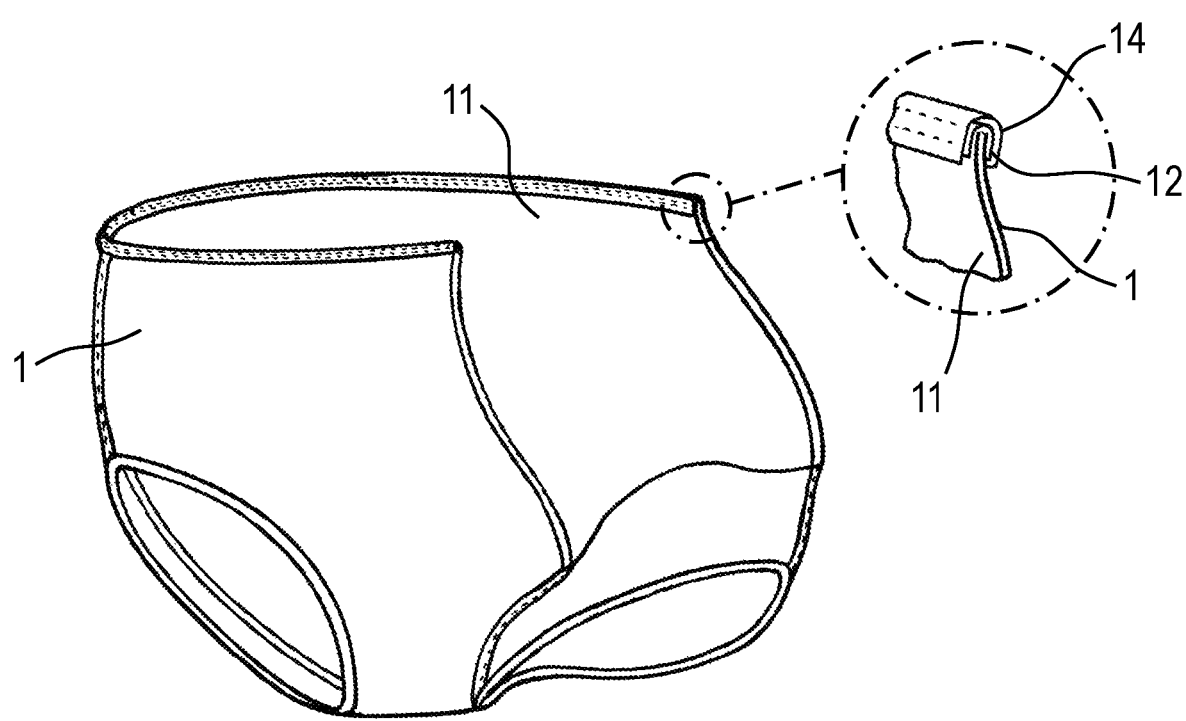
Figure 9:
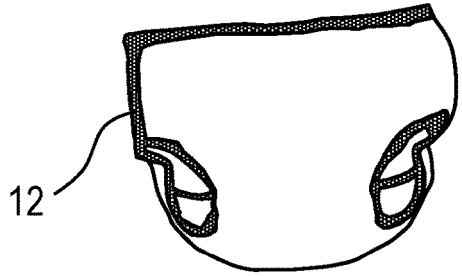
Figure 10:
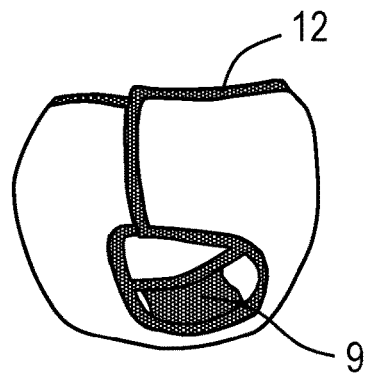
Figure 11:
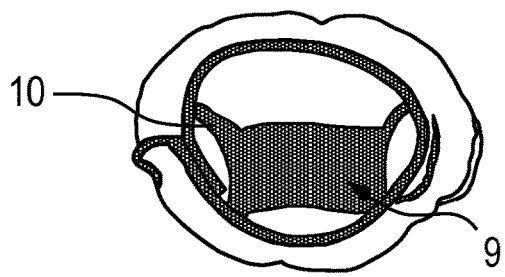
Figure 12:
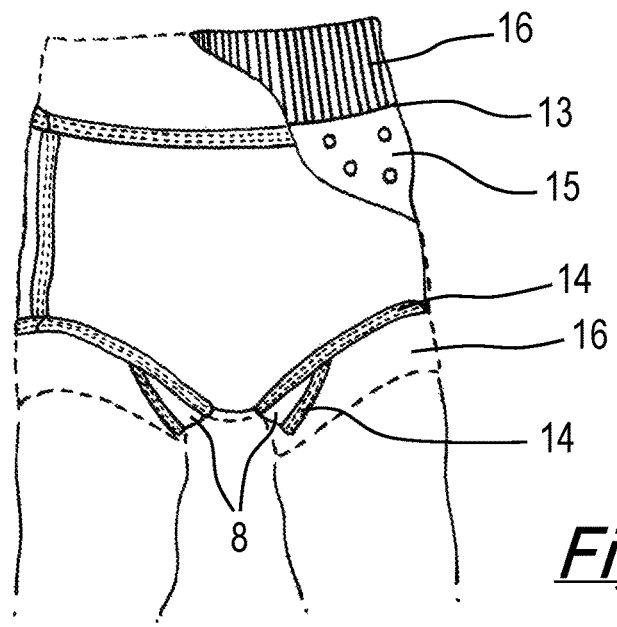
Figure 13:
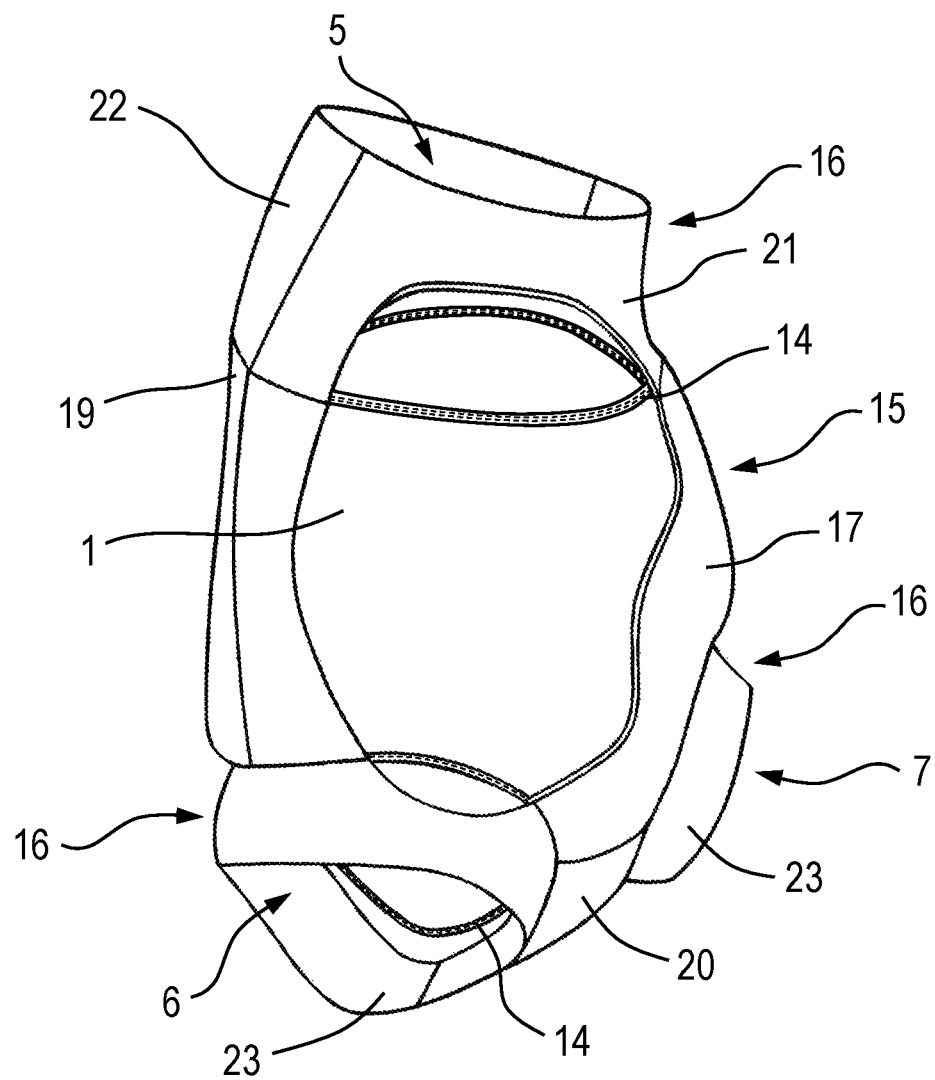
Figure 14:
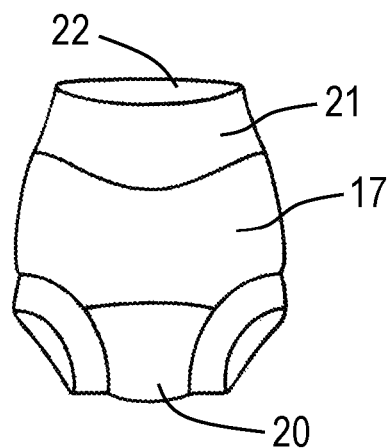
Figure 15:
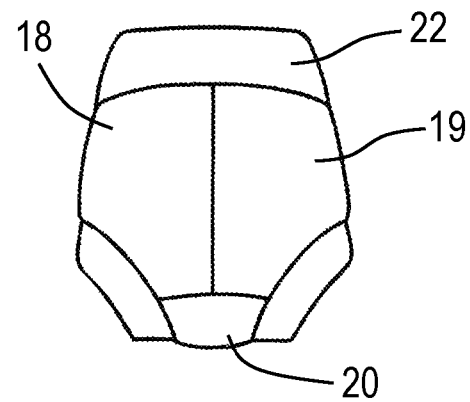
Figure 16:
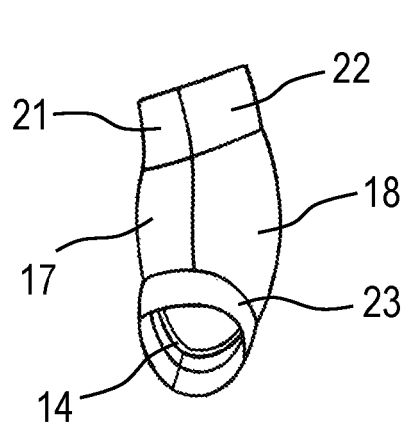
Figure 17:
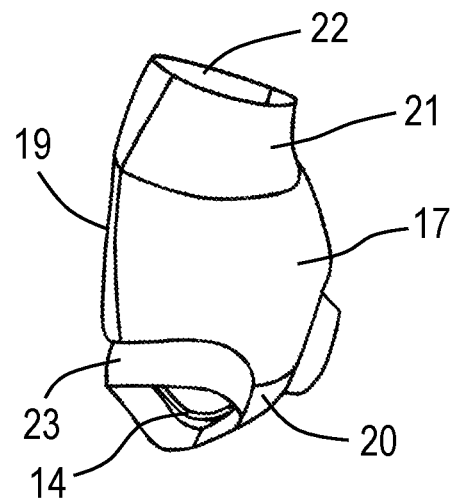
Figure 18:
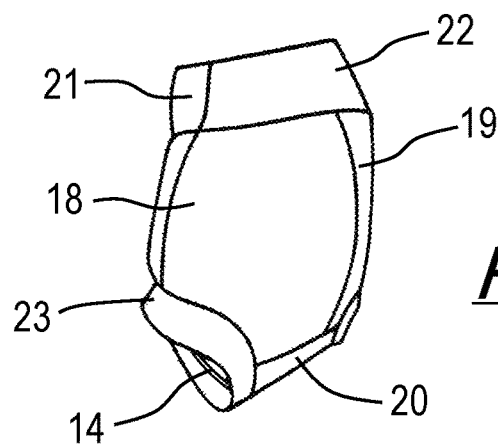
Figure 19:
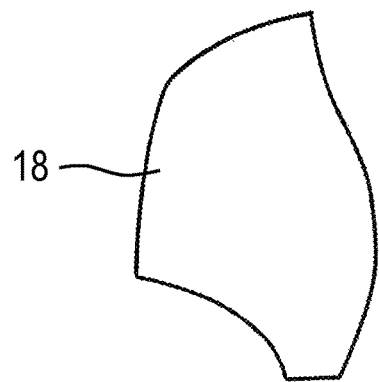
Figure 20:
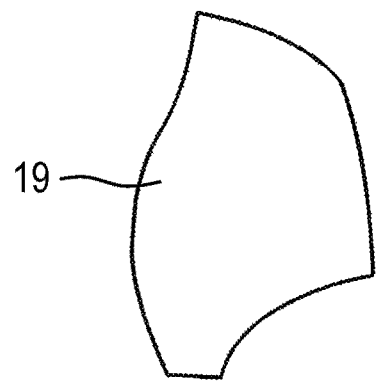
Figure 21:
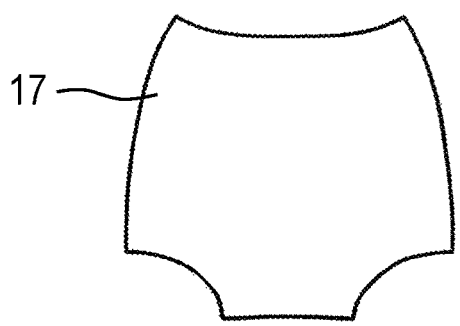
Figure 22:
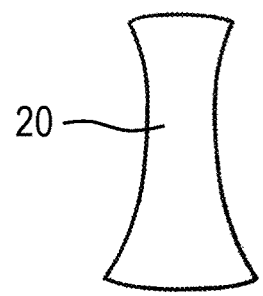
Figure 23:
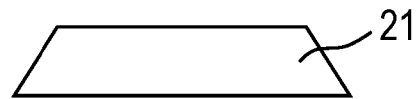
Figure 24:
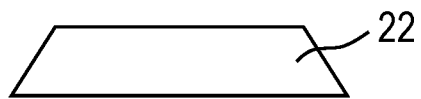
Figure 25:
Figure 26:
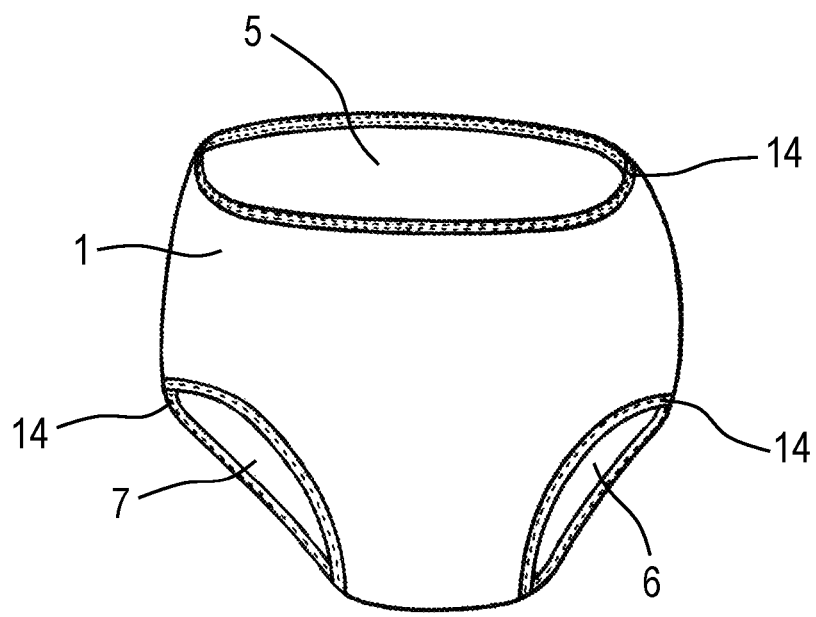
Figure 27:
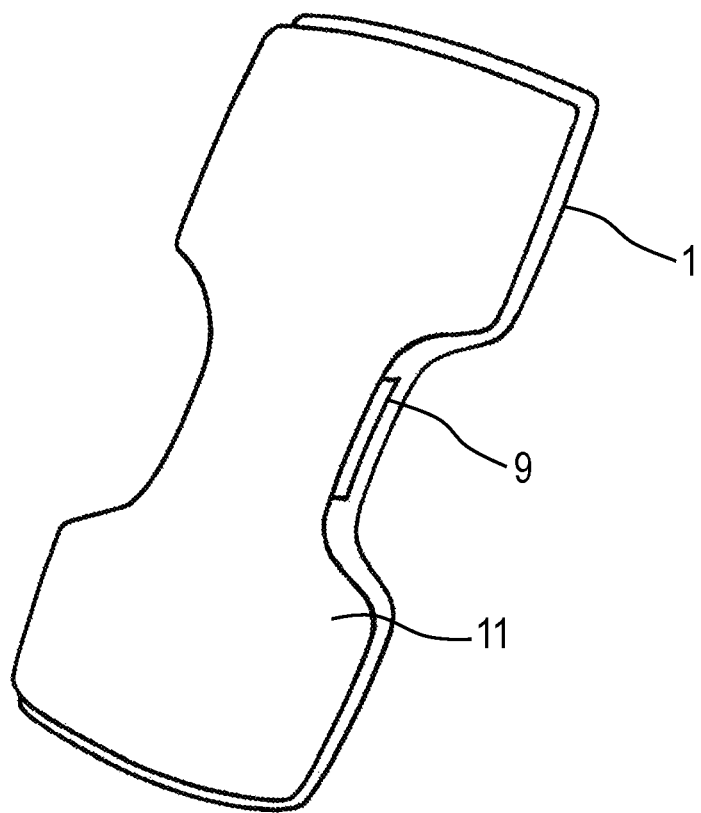

In order that the invention may be more clearly understood embodiments thereof will now be described, by way of example only, with reference to the accompanying drawings, of which:

FIG. 1 is a front view of a brief;
FIG. 2 is a rear view of the brief of FIG. 1;
FIG. 3 is a left side view of the brief of FIG. 1;
FIG. 4 is a right side view of the brief of FIG. 1;
FIG. 5 is a left side view of the brief of FIG. 1 with the left side of the brief opened;
FIG. 6 is a plan view of the brief of FIG. 1;
FIG. 7 is an underneath view of the brief of FIG. 1;
FIG. 8 is a part cut away front perspective view of the brief of FIG. 1, with an enlarged view of a circled region;
FIG. 9 is a front view of the brief of FIG. 1 with the inner textile and binding removed to reveal the antimicrobial textile;
FIG. 10 is a left side view of the brief of FIG. 9;
FIG. 11 is a plan view of the brief of FIG. 9;
FIG. 12 is a part cut-away view of the brief of FIGS. 1-11 in use worn by a by a user under a swim nappy;
FIG. 13 is a part cut-away perspective view of another swim nappy;
FIG. 14 is a front view of the swim nappy of FIG. 13;
FIG. 15 is a rear view of the swim nappy of FIG. 13;
FIG. 16 is a side view of the swim nappy of FIG. 13;
FIG. 17 is a perspective view, from the front, of the swim nappy of FIG. 13;
FIG. 18 is a perspective view, from the rear, of the swim nappy of FIG. 13;
FIG. 19 shows a rear panel of the swim nappy of FIG. 13;
FIG. 20 shows the other rear panel of the swim nappy of FIG. 13;
FIG. 21 shows the front panel of the swim nappy of FIG. 13;
FIG. 22 shows the crotch panel of the swim nappy of FIG. 13;
FIG. 23 shows the front panel of the waist band of the swim nappy of FIG. 13;
FIG. 24 shows the rear panel of the waist band of the swim nappy of FIG. 13;
FIG. 25 shows a leg band of the swim nappy of FIG. 13;
FIG. 26 is a front perspective view of a liner which forms part of the swim nappy of FIG. 13; and
FIG. 27 is an opened and exploded view showing the three textile layers comprised in the liner of FIG. 26.

In what follows the terms top, bottom, side, inside, outside, front and rear are used to describe the garments in the orientation shown in the figures, which is the orientation they would adopt when worn by a person standing upright, and should not be taken to be otherwise limiting. Corresponding reference numerals are used to denote the same or equivalent features throughout the drawings. The drawings are not to scale.

Referring to FIGS. 1 to 11 of the drawings, there is shown a garment in the form of a brief. The brief is intended to be worn as swimwear or as a liner under swimwear or a swim nappy by babies and very young children, to serve as a nappy or diaper. The brief could, however, be used by older children and adults suffering from bowel incontinence.

The brief comprises outer, inner, intermediate and binding textiles.

In this example the outer textile is woven from 70 denier nylon fully drawn yarn and has a thread count of 190. The outer textile is substantially impermeable to water. The outer textile acts to contain matter in the brief during use.

The inner textile is knitted from 50 denier 72 filament polyester yarn and has a mass of about 125 grams per square metre. The textile is permeable, and soft to the touch. The inner textile provides a soft feel to the wearer's skin making the brief comfortable to wear. It also allows fluids to pass through, such as water containing dissolved faecal matter, but not solids above a certain size, thus helping retain them within the brief.

The intermediate textile is knitted from multifilament polyester yarn of 150 denier and has a mass of 130 grams per square metre. After knitting, the textile has been coated on both sides with Silver using a vacuum deposition process, involving sputtering of substantially pure Silver to deposit Silver ions onto the textile, so that Silver makes up about 2% of the weight of the textile. It is found that particles of Silver deposited by the deposition process combine to form a coating on the surface of the fibres forming the textile. When subjected to a test for colour fastness under the action of human sweat according to ISO 105-E04:2013, testing with acid sweat (second solution) this yielded a concentration of 32 ppm of Silver. The intermediate textile has antimicrobial properties and acts to kill or prevent reproduction of bacteria and/or other pathogens.

The binding textile is a resiliently stretchable textile knitted from 82% nylon and 18% elastane with a mass of about 185 grams per square meter.

The outer shell of the brief is formed from a single panel 1 of the outer textile. Edges of the panel are stitched together along the right side of the brief at 2. To the left side of the brief the two panels overlap and are releasably fastened together by panels of hook and loop tape 3, 4 or other suitable fastening medium on the facing inside and outside overlapping surfaces of the brief. Being able to fasten and unfasten the brief along one side facilitates putting the brief on and removing it from a wearer. The outer shell defines a waist 5 and two leg 6, 7 openings. A crotch portion extends between the two leg openings.

Inner leg panels 8 with an outer surface formed from the outer textile are fastened just inside the edge of the leg openings 6, 7 along approximately the lower half of each opening. Each leg panel has a convex curved side which is stitched to the leg opening opposing a substantially straight, free edge. In an alternative embodiment the inner leg panels 8 are omitted.

A generally rectangular strip 9 of the intermediate textile is disposed over the inside of the crotch region, and respective panels of intermediate textile 10 are disposed over the inside of each inner leg panel 8, having substantially the same shape as the leg panels.

A single panel 11 of the inner textile is disposed over the entire inside of the brief.

Elongate generally rectangular strips 12 of the intermediate textile are folded along their centreline over the edges of the waist and leg openings, providing a band of intermediate textile adjacent each side of the edges of the brief surrounding the openings. Further elongate rectangular strips 12 of the intermediate textile are folded over the free ends of the inner leg panels 8 and a rectangular strip of intermediate textile extends along the inside edge of one portion of the hook and loop tape.

Elongate generally rectangular strips 14 of the binding textile of slightly greater width than those of the intermediate textile are folded along their centreline over the strips of intermediate textile in a stretched state and two generally parallel lines of stitching are formed through the binding textile. The stitching secures opposed sides of the strip of binding textile together along with strips of intermediate textile, and layers of outer, inner and, where present, intermediate textile between the opposed sides of the strip of binding textile. This holds the various panels and strips of textile together forming the brief and provides elasticated, stretchable, leg and waist openings. Binding textile is also stitched over the strip of intermediate textile which borders the hook and loop tape, securing the hook and loop tape in position.

In use, the brief is sized to fit a wearer, with the elasticated waist and leg openings and elasticated edges of the leg panels gripping the wearer's waist and legs. Optionally, the brief may we worn underneath a conventional type of swim nappy as shown in FIG. 12. FIG. 12 shows a conventional swim nappy 13 largely cut away to reveal an inner brief as shown in FIGS. 1 to 11. The swim nappy 13 is of the type described in WO2018/083474, having a body 15 formed from panels of impermeable material, such as neoprene, defining waist and leg openings around which extend elasticated bands 16. In use the swim nappy covers the wearer's body between waist and thighs. In particular, the top edge of the waist band and bottom edges of the leg bands, and preferably a major part of each band, extends beyond the waist and leg openings of the inner brief.

In use, the substantially impermeable outer shell of the brief serves to contain both liquid and solid matter within the brief. Any passage of liquids or other matter out of (or in to) the brief must take place via the leg and or waist openings, since these are not sealed to the wearer. Liquid and dissolved matter contained within the brief will come into contact with the Silver coated intermediate textile in the crotch region of the brief. The Silver coating has an antimicrobial action and will kill or inhibit reproduction of bacteria or other pathogens contained in liquid or materials into which it comes into contact. Silver from the coating may also disperse into liquid contained in the brief. For the Silver coating and any dispersed Silver to effectively treat liquid and material it must typically be exposed to the material for a period of time, possibly up to about 5 minutes. It is therefore useful that the brief substantially contains matter, increasing the probability that it is effectively treated by the Silver coating and in this respect the elasticated leg and waist openings help to retain liquid and solid matter in the brief. Ultimately, though, as the openings are not fully sealed to the wearer they will allow passage of some matter into and out of the brief, principally swimming pool water which will disperse or dissolve faecal matter, contaminating the water, which may then flow back out of the brief. Since the intermediate textile is disposed around the waist and leg openings liquids and other materials passing out of, or in to, the garment must pass through (or closely adjacent) the textile bringing it into contact the Silver coating increasing the probability that the active antimicrobial effect of the Silver may kill or inhibit reproduction of bacteria or other pathogens contained in the liquid or materials which has not already been treated whilst contained within the brief.

The brief may be washed and re-used repeatedly. It is found the repeated washing over, say, a six month period does not significantly reduce the effectiveness of the Silver coating as an antimicrobial agent. Six months is the typical useful life of swimwear for babies and young children as over that period they typically grow sufficiently to require a larger size of garment.

Where the brief is worn under a conventional swim nappy this will further help contain matter and so maximise the probability that it is treated by the Silver coating of the intermediate textile, and rendered harmless, before passing into the swimming pool through pool water flowing into and out of the swim nappy and brief via waist and leg openings.

Referring now to FIGS. 13 to 27 there is shown a swim nappy. The swim nappy comprises an outer garment, generally 15, and an inner garment in the form of a brief, both defining a single waist 5 and two leg 6, 7 openings.

The outer garment comprises a main body formed from a single front panel 17, two rear panels 18 and 19, a crotch panel 20. These panels are all substantially impermeable and formed from an approximately 1 mm thick layer of neoprene laminated between two layers of synthetic woven fabric such as a polyester or nylon fabric. Owing to inclusion of the layer of neoprene the fabric is resiliently stretchable. The panels are further described below and are joined together to form a garment having waist and leg openings, the leg openings each extending at about a 45 degree angle to the waist opening.

Resiliently stretchable waist 21, 22 and leg 23 bands extend around each opening. The waist and leg bands are formed from a resiliently stretchable knitted fabric comprising a proportion of elastic fibre. In the described example the fabric is a tricot knit fabric formed from approximately 70% nylon and 30% elastane (spandex) fibres. This fabric has a greater degree of elasticity than the fabric forming the panels of the main body of the brief.

The front panel 17 has top, bottom and two side edges on opposite sides of the panel. It is symmetric about a vertical centre line extending between the top and bottom edges. The opposed side edges are generally convex, and taper towards each other towards the top edge. The side edges meet the top edge at an approximate right angle. The bottom edge is formed from two concave curves extending respectively at an approximate right angle from the bottom of each side edge and each meeting a central substantially straight section at an approximate right angle.

The two rear panels 18, 19 each have top and bottom edges and opposed outer and inner side edges which are mirror opposites of each other. The top and outer edges are convex. The outer edge is substantially the same length as the outer edges of the front panel 17. The top edge meets the outer edge at an obtuse angle. The opposite end of the top edge meets the inner edge at an approximate right angle. The inner edge is slightly concave adjacent the top edge and transitions into a convex shape, such that over its length the inner edge has the general shape of a full wave. The inner edge is longer than the outer edge. The bottom edge has a substantially straight portion which meets the inner edge at an obtuse angle, and a concave portion which extends from the opposite end of the straight portion to the lower end of the outer edge. The concave portion meets both the straight portion and the outside edge at obtuse angles. The height of the panel from the bottom edge to the top edge increases from the outer edge to the inner edge of the panel.

The crotch panel 20 has convex front and rear edges joined by concave sides and is symmetric about a centre line running between the front and rear edges. The front edge is the same length as the central substantially straight portion of the lower edge of the front panel 17, and the length of the rear edge is double that of the substantially straight portion of the lower edge of one rear panel 18, 19.

The waist band is formed from substantially identical front 21 and rear 22 panels, each being substantially trapezoidal in shape, having substantially parallel upper and lower edges, with the upper edge shorter than the lower edge. The height of each panel between its parallel sides is the same, about 6 cm in the current example.

The leg bands 23 are each formed from a single, elongate, generally rectangular panel of fabric, with a width of about 4 cm in the current example.

To form the outer garment the inner edges of the rear panels 18, 19 are stitched together with their respective ends aligned, the outer edge of each rear panel is stitched to a respective side of the front panel 17, again with their ends aligned. The front edge of the crotch panel 20 is stitched to the central substantially straight portion of the lower edge of the front panel 17 and the rear edge is stitched to the adjacent straight portions of the lower edge of the rear panels 18, 19. The panels are all stitched together with flat lock stitching, so that the edges of adjacent, joined panels abut each other. This forms the main body of the outer garment.

The lower edge of the front panel 21 of the waist band is stitched to the top edge of the front panel 17 with the respective ends of the edges aligned. Similarly, the lower edge of the rear panel 22 of the waist band is stitched to the combined top edges of the two rear panels 18, 19. The panels 21, 22 of the waist band are stitched to front 17 and rear 18, 19 panels of the garment by way of internal seams. Respective sides of each panel 21, 22 of the waist band are stitched together with flat lock stitching to form a continuous loop. As the panels 21, 22 making up the waist band are trapezoidal the length of the top, free edge of the waist band is longer than the bottom edge, which is fastened to the main body of the garment. The height of the panels 21, 22 forming the waist band, from their bottom edge to top edge, is a minimum of about 25% of the overall height of the garment from the top edge of the waist band to the underside of the crotch panel.

A long edge of each leg band 23 panel is stitched around each leg opening formed by an outer concave portion of the lower edge of the front panel 17, the concave portion of the lower edge of the adjacent rear panel 18, 19 and the adjacent side of the crotch panel 20. The long edge of the leg band 23 panel is the same length as the combined length of the edges of other panels to which it is stitched so the leg band completely encircles the leg opening. Opposite short ends of the leg band panel are then stitched together to form a continuous band.

The inner, brief, is essentially the same as the brief illustrated in FIGS. 1 to 11 being formed form the same materials and having essentially the same construction. The inner brief differs from the brief illustrated in FIGS. 1 to 11 only in the following ways.

Adjacent edges of the single textile panels forming the outer shell 1 and inner lining 11 are stitched to together along both the left and right hand sides of the garment, so the garment cannot be opened to one side. There are no inner leg panels. And the brief is stitched into the outer garment. This is achieved by bottom edges of the panels 21, 22 forming the waist band, and the top edges of the front 17 and rear 18, 19 panels of the outer garment, extending and being stitched into the binding material 14 which extends around the waist opening of the brief, together with the top edges of the textile panels 1, 11 forming the outer shell and inner lining of the brief. A line of stitching extends through the binding material and the materials captured within it to form an elasticated seam connecting the inner and outer garments.

The inner brief and outer garment are shaped and positioned relative to each other so that the leg openings of the brief are adjacent to or just inside the leg openings defined by the main body of the outer garment. The combination can thus be comfortably worn as a single garment which gives the advantages of the two garment combination shown in FIG. 12 but which can be put on and taken off a user more easily. Since the inner brief is only attached to the outer garment around the waist the bulk of the inner brief can be turned inside out to extend out of the waist of the outer garment to facilitate washing.

The above embodiments are described by way of example only. Many variations are possible without departing from the scope of the invention.

The invention claimed is:

1. A swimwear adapted, in use, to cover a wearer's body between the waist and thighs, the swimwear comprising a shell of liquid impermeable material, a permeable inner lining material which lies next to the wearer's skin in use, an antimicrobial agent disposed between the shell of liquid impermeable material and the inner lining material, the swimwear taking the form of a brief having waist and leg openings and the swimwear comprising elongate rectangular strips of an intermediate textile folded along their centreline over edges of the waist and leg openings, the intermediate textile having antimicrobial properties wherein the antimicrobial agent is disposed on a textile material which is knitted.

2. A swimwear as claimed in claim 1 wherein the shell is formed from a textile material.

3. A swimwear as claimed in claim 1 wherein the inner lining material is formed from a textile material.

4. A swimwear as claimed in claim 1 wherein the antimicrobial agent is inorganic.

5. A swimwear as claimed in claim 4 wherein the antimicrobial agent is a metal.

6. A swimwear as claimed in claim 5 wherein the antimicrobial agent is silver.

7. A swimwear as claimed in claim 1 wherein the antimicrobial agent is coated onto the textile material by a physical deposition process.

8. A swimwear as claimed in claim 1 wherein the antimicrobial agent makes up at least 1% by weight of the textile material.

9. A swimwear as claimed in claim 1 wherein the textile material is formed from multifilament yarn of between 130 and 170 Denier.

10. A swimwear as claimed in claim 1 wherein the textile has a mass in the range 100 to 150 grams per square meter.

11. A swimwear as claimed in claim 1 wherein the textile is positioned at least within a crotch region of the garment and/or adjacent waist and leg openings of the garment.

12. A swimwear as claimed in claim 11 wherein the waist and leg openings are elasticated.

13. A method of manufacture of swimwear comprising the steps of:
   a. providing a yarn or textile;

b. coating said yarn or textile with an antimicrobial agent using a physical deposition process;
c. where present, forming the yarn into a textile; and
d. forming a swimwear which includes the coated textile; wherein the coated textile material is formed from multifilament yarn of between 130 and 170 Denier and/or has a mass in the range 100 to 150 grams per square meter.

14. A method as claimed in claim 13 wherein the antimicrobial agent is silver.

15. A method as claimed in claim 14 wherein the coated textile comprises at least 1% by weight of silver.

16. A method as claimed in claim 13 wherein the coated textile is positioned at least within a crotch region of the swimwear and/or adjacent waist and leg openings of the swimwear.

17. A method as claimed in claim 13 wherein the swimwear is intended, in use, to cover a wearer's body between the waist and thighs and comprises a shell of liquid impermeable material, a permeable inner lining material which lies next to the wearer's skin in use and wherein the coated textile is disposed between the shell of liquid impermeable material and the inner lining material, the swimwear taking the form of a brief having waist and leg openings and the swimwear comprising elongate rectangular strips of an intermediate textile folded along their centreline over edges of the waist and leg openings, the intermediate textile having antimicrobial properties.

18. A method as claimed in claim 13 wherein the swimwear comprises a shell of liquid impermeable material and a permeable inner lining material which lies next to the wearer's skin in use and wherein the coated textile is disposed between the shell of liquid impermeable material and the inner lining material.

19. A method of reducing contamination of a swimming pool by a swimmer comprising: the swimmer wearing a swimwear, adapted, in use, to cover a wearer's body between the waist and thighs, the swimwear comprising a shell of liquid impermeable material, a permeable inner lining material which lies next to the wearer's skin in use, an antimicrobial agent disposed between the shell of liquid impermeable material and the inner lining material, the swimwear taking the form of a brief having waist and leg openings and the swimwear comprising elongate rectangular strips of an intermediate textile folded along their centreline over edges of the waist and leg openings, the intermediate textile having antimicrobial properties
and wearing a swim nappy over that swimwear, the swim nappy comprising a body of liquid impermeable material and elasticated waist and leg bands.

* * * * *